US00PP18826P2

(12) United States Plant Patent
Gravois et al.

(10) Patent No.: US PP18,826 P2
(45) Date of Patent: May 20, 2008

(54) SUGAR CANE VARIETY NAMED 'L99-233'

(50) Latin Name: ***Saccharum* sp.**
Varietal Denomination: L99-233

(75) Inventors: Kenneth A. Gravois, Baton Rouge, LA (US); Keith P. Bischoff, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 1 day.

(21) Appl. No.: 11/599,970

(22) Filed: Nov. 15, 2006

(51) Int. Cl.
*A01H 5/00* (2006.01)

(52) U.S. Cl. ..... Plt./258
(58) Field of Classification Search ..... Plt./258
See application file for complete search history.

(56) References Cited

U.S. PATENT DOCUMENTS

PP10,839 P 3/1999 Holder
PP12,710 P2 6/2002 Holder
2006/0150291 P1 7/2006 Gravois

OTHER PUBLICATIONS

Bischoff, K.P. et al., "The Development of New Sugarcalce Varieties at the LSU AgCenter," J. Amer. Soc. Sugar Technol., vol. 24, pp. 142–164 (2004).

Legendre, B.L. et al., "Registration of 'HoCP85–845' Sugarcane," Crop Sci., vol. 34, p. 820 (1994).

Legendre, B.L. et al., "Registration of 'HoCP91–555' Sugarcane," Crop Sci., vol. 40, p. 1506 (2000).

Legendre, B.L. et al., "The 2003 Louisiana Sugarcane Variety Survey," Sugar Bulletin, vol. 82(9), pp. 22–28 (2004).

Milligan, S.B. et al., "Registration of 'LCP 85–384' Sugarcane," Crop Sci., vol. 34, pp. 819–821 (1994).

Tew, T.L. et al., "Registration of 'HoCP96–540' Sugarcane," Crop Sci., vol. 44, pp. 785–786 (2005).

*Primary Examiner*—Wendy C Haas
(74) *Attorney, Agent, or Firm*—John H. Runnels; Bonnie J. Davis; James C. Carver

(57) ABSTRACT

A new variety of sugarcane, identified as 'L99-233', is disclosed having superior sugarcane rust disease resistance, excellent ratooning ability, and high sugar/sucrose content and cane yield characteristics.

5 Drawing Sheets

Genus and species name: *Saccharum* sp.
Variety denomination: 'L99-233'.
This invention pertains to a new and distinct variety of sugarcane.

BACKGROUND OF THE INVENTION

Sugarcane variety, *Saccharum* sp., is a giant, thick, perennial grass of the Gramineae family cultivated in tropical, subtropical, and some temperature regions worldwide for its sweet sap, which is a major source of sugar and molasses. Sugarcane is believed to have originated in what is now known as New Guinea.

SUMMARY OF THE INVENTION

This new and distinct sugarcane variety, *Saccharum* sp., demonstrates superior sugarcane rust disease resistance, excellent ratooning ability, and high cane yield characteristics as compared to other available sugarcane varieties known to the inventors. A new variety of sugarcane identified as 'L99-233' is disclosed having high cane yield, excellent ratooning ability, high sucrose content, and resistance to sugarcane rust disease.

This new and distinct sugarcane variety is identified as 'L99-233', and is characterized by its greenish stalk.

BRIEF DESCRIPTION OF THE DRAWINGS

The file of this plant contains at least one photograph executed in color. Copies of this patent or patent application publication with color drawing(s) will be provided by the Office upon request and payment of the necessary fee.

DETAILED BOTANICAL DESCRIPTION

Figure 1:
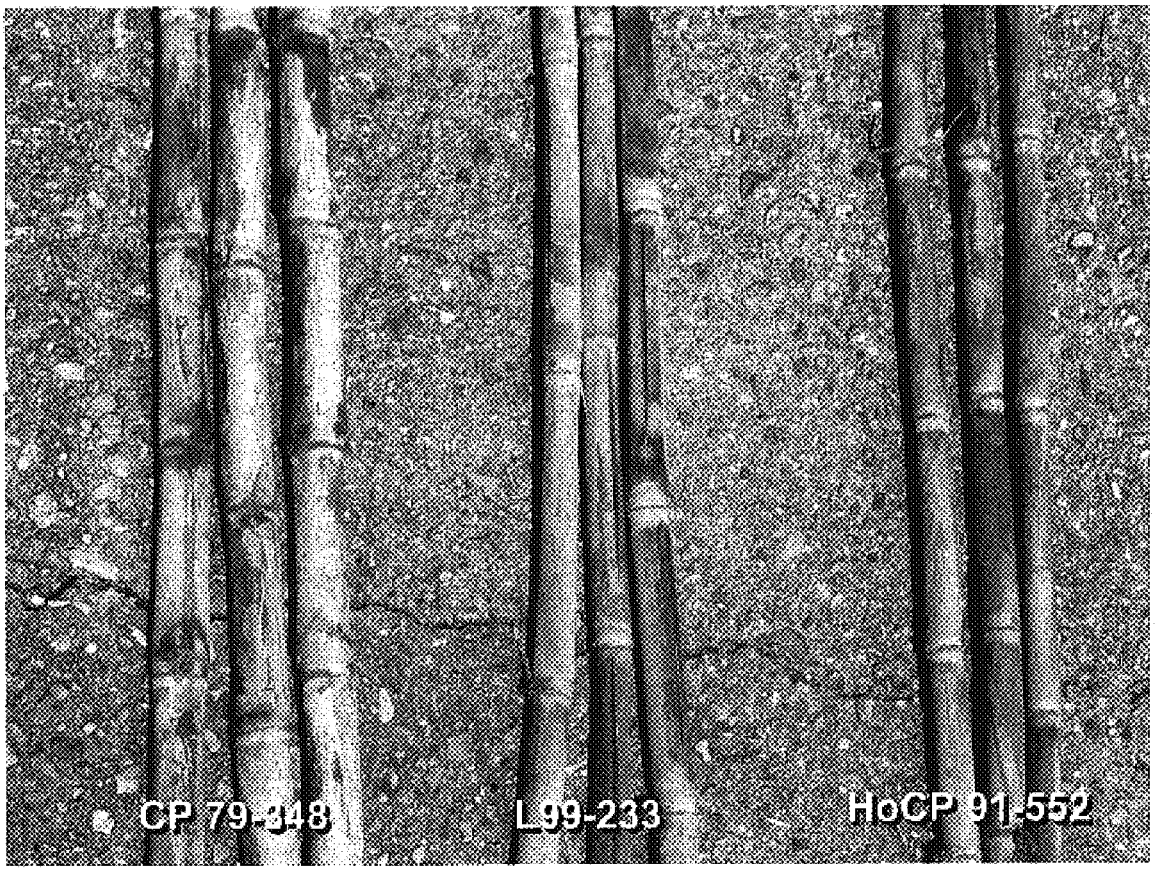
FIG. 1 is a color photograph of the stalk of the novel variety of sugarcane identified as 'L99-233' and other sugarcane varieties identified as 'CP79-348' and 'HoCP91-552', which were used for comparison tests.

This new variety of sugarcane, identified as 'L99-233', originated as a true seedling, produced by a biparental cross (identified by the inventors as 'XL94-8' (unpatented)) between the female parent 'CP79-348' (unpatented) and the male parent 'HoCP91-552' (unpatented)). In this form of variety designation, which is well known among sugarcane breeders, the "L" indicates the cross and selection occurred in the sugarcane breeding program in St. Gabriel, La. The "99" indicates the year of assignment of a permanent variety identification, and "233" is a unique number assigned to varieties that year. The cross was made in 1994 in St. Gabriel, La., and this new variety was selected from among the progeny of the cross. Early stage selection among the progeny was done between the years 1994 and 1998. The seedling of 'L99-233' was germinated from a "true seed" in January, 1995 and transplanted to the field in April, 1995. Selection occurred in the first ratoon crop in 1996 from a single stool of sugarcane. Two stalks were cut and transplanted successfully for asexual reproduction. Asexual propagation of the new cultivar by cuttings has shown that the unique features of this new sugarcane are stable and the plant reproduces true to type in successive generations of asexual propagation. Plants described herein were characterized on Sep. 11–19, 2006 at approximately 160–175 days in age from spring emergence. The stalks characterized were from inner rows unexposed to direct sunlight. See K. P. Bischoff, et al., "The Development of New Sugarcane Varieties at the LSU AgCenter," *J. Amer. Soc. Sugar Technol.,* vol. 24, pp. 142–164 (2004).

Neither 'CP79-348', the male parent, not 'HoCP91-552', the female parent, ever attained commercial status, but both have been used as parents in the sugarcane breeding program in St. Gabriel, La. The male parent, 'CP79-348', exhibits high cane yield, is below commercial standards for sucrose content, and has good ratooning ability. The female parent, 'HoCP91-552', exhibits high cane yield and sucrose characteristics, but possesses a higher fiber content compared to its new progeny. 'L99-233' was developed to provide a new variety with characteristics similar to 'LCP85-384' (the predominent commercial sugarcane variety in Louisiana), but with improved sugarcane rust resistance, and high can yield and sucrose content, similar to the female parent, 'HoCP91-552'.

'L99-233' is characterized by a greenish stalk. See B. L. Legendre, et al., "The 2005 Louisiana Sugarcane Variety Survey," *Sugar Bulletin,* vol. 84(9), pp. 28–31 (2006). Color terminology used herein is in accordance with the MUNSELL® color charts for plant issue and the MUNSELL® Book of Color for stalk and leaf determination (Munsell Color, Gretag Macbeth LLC, New Windsor, N.Y. The color descriptions and color illustrations are as nearly true as is reasonably possible. However, it is understood that both color and other phenotypic expressions described herein may vary from plant to plant with differences in growth, environment and cultural conditions, without any change in the genotype of the variety 'L99-233'.

FIG. 1 depicts stalks of 'L99-233', its female parent 'CP79-384', and male parent 'HoCP91-552'. A moderate white wax bloom covers the stalks of 'L99-233' and 'HoCP91-552', and an extensive white wax bloom covers the stalks of 'CP79-348'. The stalk color of each variety varies under a wax bloom (unexposed to sunlight). 'L99-233' exhibits a greenish stalk [10Y (Yellow) 6/4] as compared to that of 'CP79-348', which has a stalk color of [10Y (Yellow) 4/4], and 'HoCP81-10', which has a stalk color of [10Y (Yellow) 7/6]. (The stalk color of each variety became more red or purple when exposed to sunlight.) Colorimetric evaluations using the aforementioned color charts of the stalk, wax, and leaf for 'CP79-348', 'HoCP91-552', and 'L99-233' at harvest, are shown in Table 1.

'L99-233' emerged quickly after planting and exhibited an average mature stalk height (ground level to the top visible dewlap) of 288 cm, as compared to the mature stalk heights of 'CP79-348' of 271 cm and of 'HoCP91-552' of 300 cm. The average stalk diameter of 'L99-233' was 21.2 mm, as compared to stalk diameters of 'CP79-348' (22.8 mm dia) and 'HoCP91-552' (22.1 mm dia).

'L99-233' and 'CP79-348' each exhibited a conoidal shaped internode, whereas 'HoCP91-552' exhibited a cylindrical shaped internode (fourth internode from ground level). 'L99-233,' 'CP79-348' and 'HoCP91-552' each had glabrous (lacking hair) growth rings with widths of 2.66 mm, 2.56 mm, and 1.74 mm, respectively. The internodes of 'L99-233' were smooth and glabrous with few, if any, corky patches or obvious growth cracks. The two parent varieties had similar internodes, but neither exhibited growth cracks. The average internode length of 'L99-233' at mid culm was 16.8 cm. The internodes of 'L99-233' and 'CP79-348' exhibited no bud furrow, whereas 'HoCP91-552' did exhibit bud furrows.

The widths of the root bands of each variety were similar, although 'CP79-348' had a slightly greater root band width. The root bands of all three varieties were glabrous with straight sides, and exhibited unequally distributed rows of irregularly-shaped root primordia having diameters of between about 0.25 and about 0.50 mm. The root bands of 'L99-233', 'CP79-348', and 'HoCP91-552' exhibited no wax layer.

The buds of each variety were located just above the leaf scar, and were raised above the surface of the root band. 'L99-233' and 'CP79-348' similarly exhibited ovate shaped buds (at the fourth node) with a central germ pore, while 'HoCP91-552' exhibited narrowly shaped ovate buds. Bud diameters of both 'L99-233' and 'HoCP91-552' were just over 5 mm, which was smaller than bud diameters of 'CP79-348'. Bud colors of 'L99-233', 'CP79-348', and 'HoCP91-552' were [7.5Y (Yellow) 7/8], [5Y (Yellow) 8/10], and [10Y (Yellow) 5/8], respectively, without any wax on the bud surfaces. None of the three varieties exhibited any setaceous or pilose hairs on the buds. See Table 1.

Figure 2:
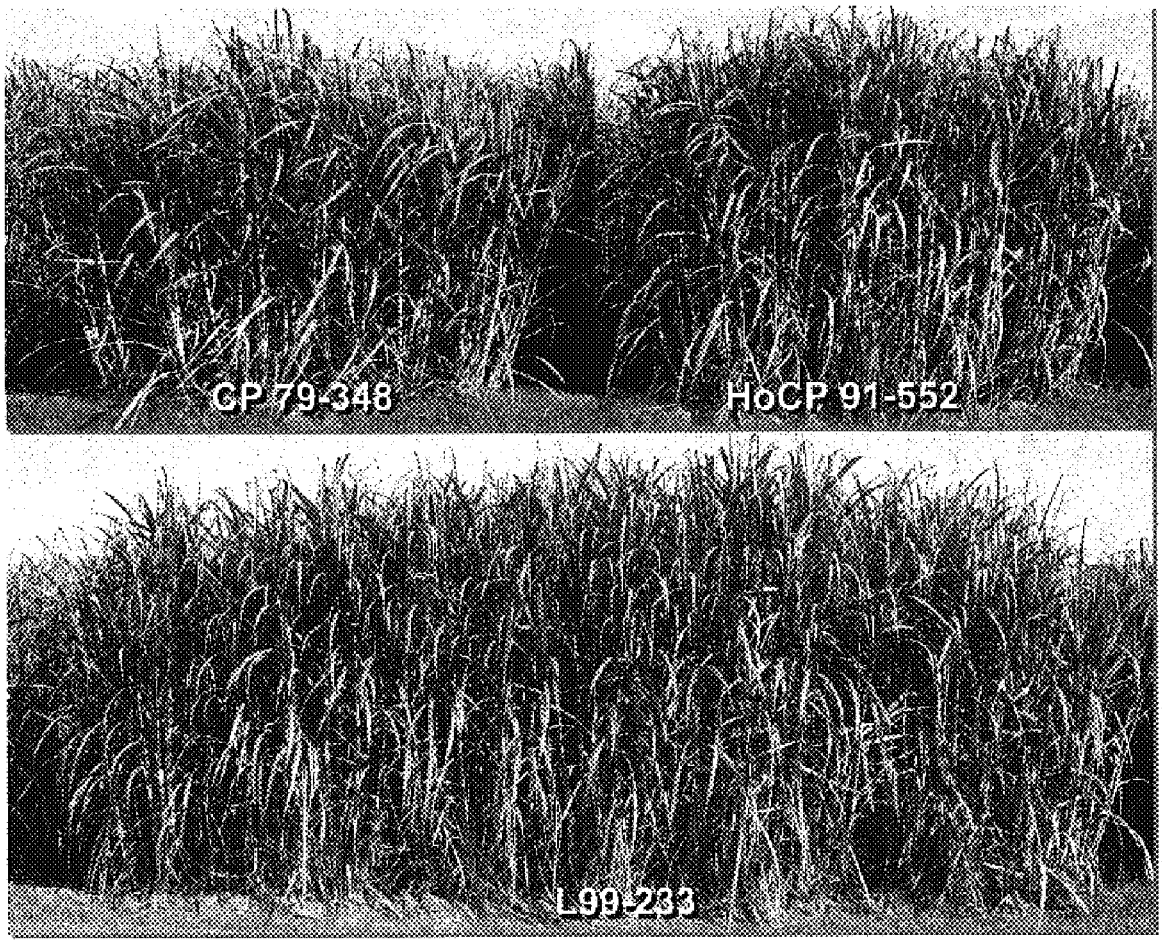
FIG. 2 is a color photograph of the canopy biomass of the novel variety of sugarcane identified as 'L99-233' and other sugarcane varieties identified as 'CP79-348' and 'HoCP91-552', which were used for comparison tests.

FIG. 2 depicts the canopy biomass of the novel variety of sugarcane identified as 'L99-233' and other sugarcane varieties identified as 'CP79-348' (unpatented) and 'HoCP91-552' (unpatented), which were used for comparison tests. The canopies of 'L99-233' and 'HoCP91-552' were drooping, while the canopy of 'CP79-348' was slightly erect.

Figure 3:
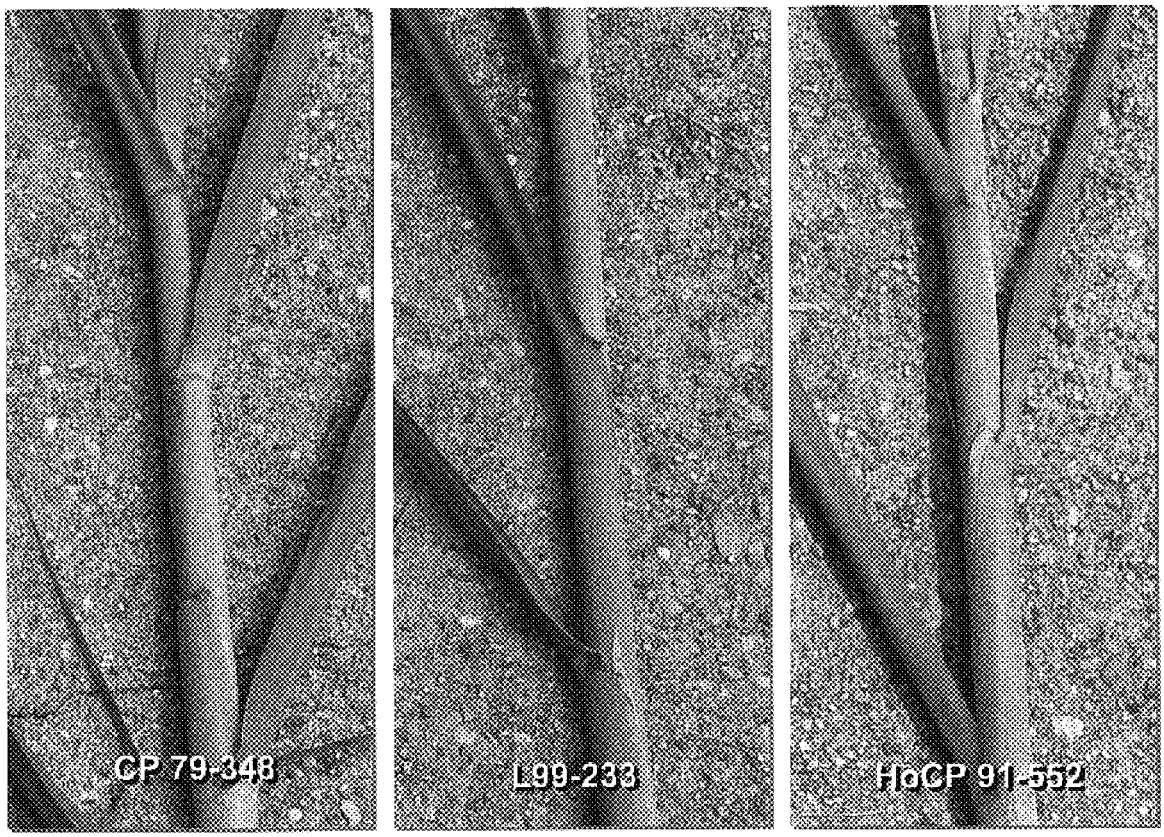
FIG. 3 is a color photograph of the leaf sheath, dewlaps (leaf colors), and auricles of the novel variety of sugarcane identified as 'L99-233' and other sugarcane varieties identified as 'CP79-348' and 'HoCP91-552', which were used for comparison tests.

FIG. 3 depicts upper leaf sheaths, dewlaps (leaf collars), and auricles of 'CP79-348', 'L99-233', and 'HoCP91-552. The average leaf blade length and width of 'L99-233', 'CP79-348', and 'HoCP91-552', at the third leaf below the top most visible dewlap, were 149 cm and 3.97 cm, 150 cm and 4.46 cm, and 149 cm and 4.01 cm, respectively. The leaf colors of 'L99-233' and 'CP79-348' were similar, as they exhibited green leaf blades [7.5 G(green) Y(yellow) 3/4] at the second visible dewlap, whereas 'HoCP91-552' exhibited a slightly different green color [7.5 G(green) Y(yellow) 4/4] at the second visible dewlap. Each of these varieties exhibited acuminate leaf blades.

'L99-233', 'CP79-348' and 'HoCP91-552' similarly exhibited 4–8 mm wide mid-ribs distinctly raised on their abaxial sides. The abaxial mid-rib colors of all three varieties were a slightly lighter green than the colors of their leaf blades. Adaxial side mid-ribs of 'L99-233' had smooth to concave surfaces, which were whitish in color [2.5GY (Green Yellow) 6/8] and lighter than their leaf blades. Both leaf blades and mid-ribs of 'L99-233' were linear, glabrous with a smooth surface and relatively thin.

Dewlaps of 'L99-233' were double crescent deltoid with a color of [2.5GY (Green Yellow) 6/6]. Both parental varieties had descending deltoid dewlap shapes. The dewlap color of 'CP79-348' was [10Y (Yellow) 5/8]; the dewlap color of 'HoCP91-552' was [2.5GY (Green Yellow) 6/8].

'L99-233' exhibited a very slightly necrotic leaf sheath margin. Auricles of 'L99-233' were necrotic. The average auricle shape for 'L99-233' was falcate. The average auricle shape for 'CP79-348' was short lanceolate, while the average auricle shape of 'HoCP91-552' was long lanceolate. Auricles were measured on the fourth leaf from the top most visible dewlap.

'L99-233' and 'HoCP91-552' both exhibited a broad crescent-shaped ligule, while 'CP79-348' exhibited a linear crescent ligule. 'L99-233' exhibited tan ligules [10YR (Yellow Red) 3/4] having lengths of about 5.16 mm and widths of about 17.9 mm. The ligule region of 'L99-233' and 'CP79-348' exhibited pubescence, whereas 'HoCP91-552' did not exhibit ligule pubescence. See Table 1.

TABLE 1

| Trait | Variety L99-233 | Female L79-348 | Male HOCP91-552 |
|---|---|---|---|
| Stalk Height (cm) Avg. 10 stalks | 288 | 271 | 300 |
| Stalk Culm Diameter (mm) Avg. 10 stalks | 21.2 | 22.8 | 22.1 |
| Leaf Shape | Drooping | Slightly Erect | Drooping |
| Leaf Length (cm) Avg. 10 leaves | 149 | 150 | 149 |
| Leaf Width (cm) Avg. 10 leaves | 3.97 | 4.46 | 4.01 |
| Flesh Color | 10Y 8.5/2 | 7.5Y 8.5/4 | 5Y 8/2 |
| Leaf Color | 7.5GY 3/4 | 7.5GY 3/4 | 7.5GY4/4 |
| Wax Color | BG-PB 9/10PB | BG-PB 9/10PB | BG-PB 9/5PB |
| Stalk Color | 10Y 6/4 | 10Y 4/4 | 10Y 7/6 |
| Stalk Buds/Shape(4th node) | Ovate | Ovate | Narrow Ovate |
| Auricle Shape | Falcate | Short Lanceolate | Long Lanceolate |
| Auricle Length (mm) Avg. 10 | 15.82 | 13.15 | 39.25 |
| INTERNODE: | | | |
| Waxiness | Moderate | Extensive | Moderate |
| Bud Furrow | None | None | Yes |
| Growth Ring Width | 2.66 mm | 2.56 mm | 1.74 mm |
| Growth Ring Surface | Glabrous | Rough | Glabrous |
| Root Band Width | 6.17 mm | 7.62 mm | 6.94 mm |
| Stalk Shape | Conoidal | Conoidal | Cylindrial |
| 4th Internode from ground level | | | |
| Internode length (cm) Avg. 10 | 16.8 | 17.5 | 16.8 |
| Ligule Shape | Broad Crescent | Linear Crescent | Broad Crescent |
| Leaf Sheath: | | | |
| Average Length (cm) Avg. 10 | 36.65 | 34.35 | 37.60 |
| Color | 10Y 614 | 2.5GY 514 | 10Y 518 |
| Leaf Scar Shape | Horizontal | Obliquely | Horizontal |
| Bud: | | | |
| Bud Diameter (mm) Avg. 10 | 5.67 | 7.69 | 5.77 |
| Bud Hair | Glabrous | Glabrous | Glabrous |

TABLE 1-continued

| Trait | Variety L99-233 | Female L79-348 | Male HOCP91-552 |
|---|---|---|---|
| Bud Color | 7.5Y 7/8 | 5Y 8/10 | 10Y 5/8 |
| Bud Wax | No | No | No |
| Leaf: | | | |
| Midrib | | | |
| Abaxial Color | 7.5Y 8.5/2 | 7.5Y 8.5/2 | 7.5Y 8.5/4 |
| Adaxial Color | 2.5GY 6/8 | 2.5GY 5/8 | 2.5 GY 5/8 |
| Dewlap Shape | double crescent deltoid | descending deltoid | descending deltoid |
| Dewlap Color | 2.5GY 6/6 | 10Y 5/8 | 2.5GY 6/8 |
| Ligule Color | 10YR 3/4 | 5YR 3/6 | 10YR 5/4 |
| Ligule Length (mm) Avg. 10 | 5.16 | 5.66 | 5.49 |
| Ligule Width (mm) Avg. 10 | 17.89 | 19.59 | 19.83 |
| Ligule Hair | Yes | Yes | No |
| Leaf Sheath Hair | Slight | Slight | None |

Figure 4:
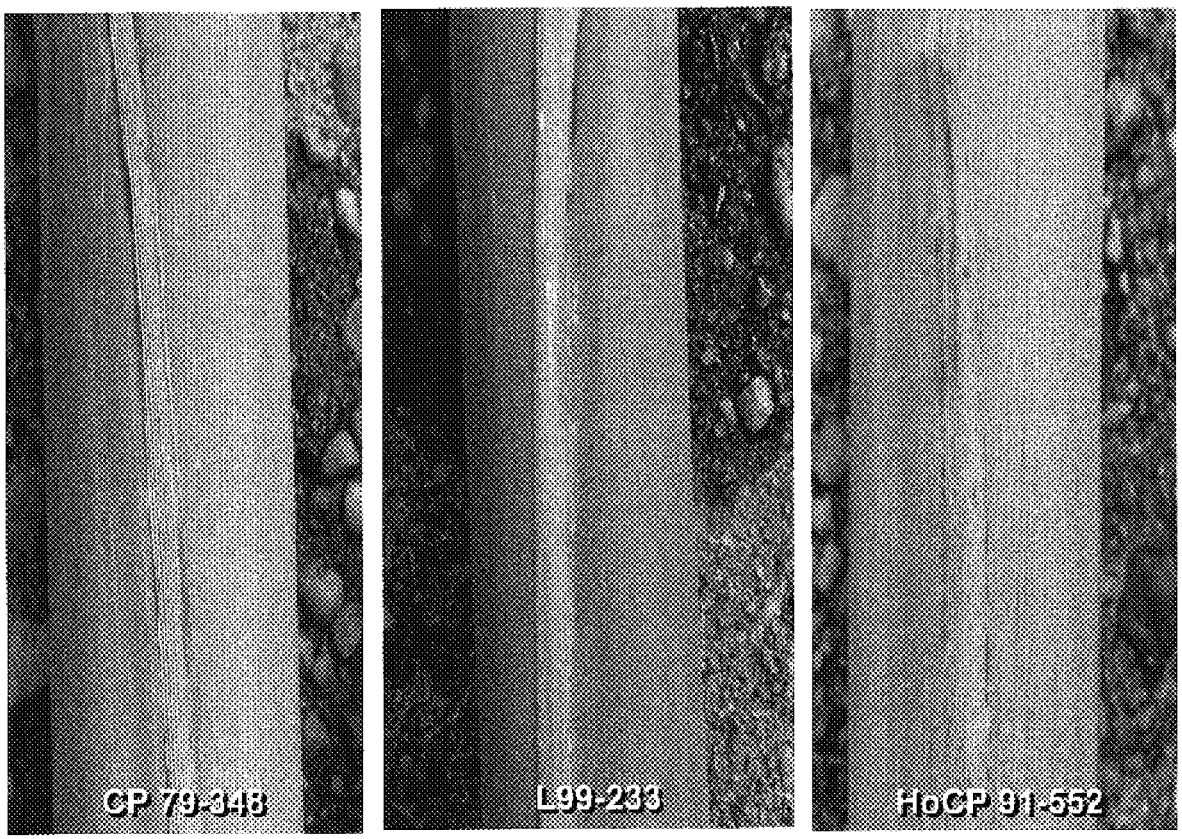
FIG. 4 is a color photograph of the leaf sheath of the novel variety of sugarcane identified as 'L99-233' and other sugarcane varieties identified as 'CP79-348' and 'HoCP91-552', which were used for comparison tests.

FIG. 4 depicts the leaf sheaths of 'CP79-348', 'L99-233', and 'HoCP91-552'. On the abaxial side of the leaf sheath, both 'CP79-348' and 'L99-233' exhibited slight amounts of setaceous hair, whereas 'HoCP91-552' was glabrous. Leaf sheath pubescences of 'CP79-348' and 'L99-233' were predominately opposite of the dewlap of the next lower leaf.

Figure 5:
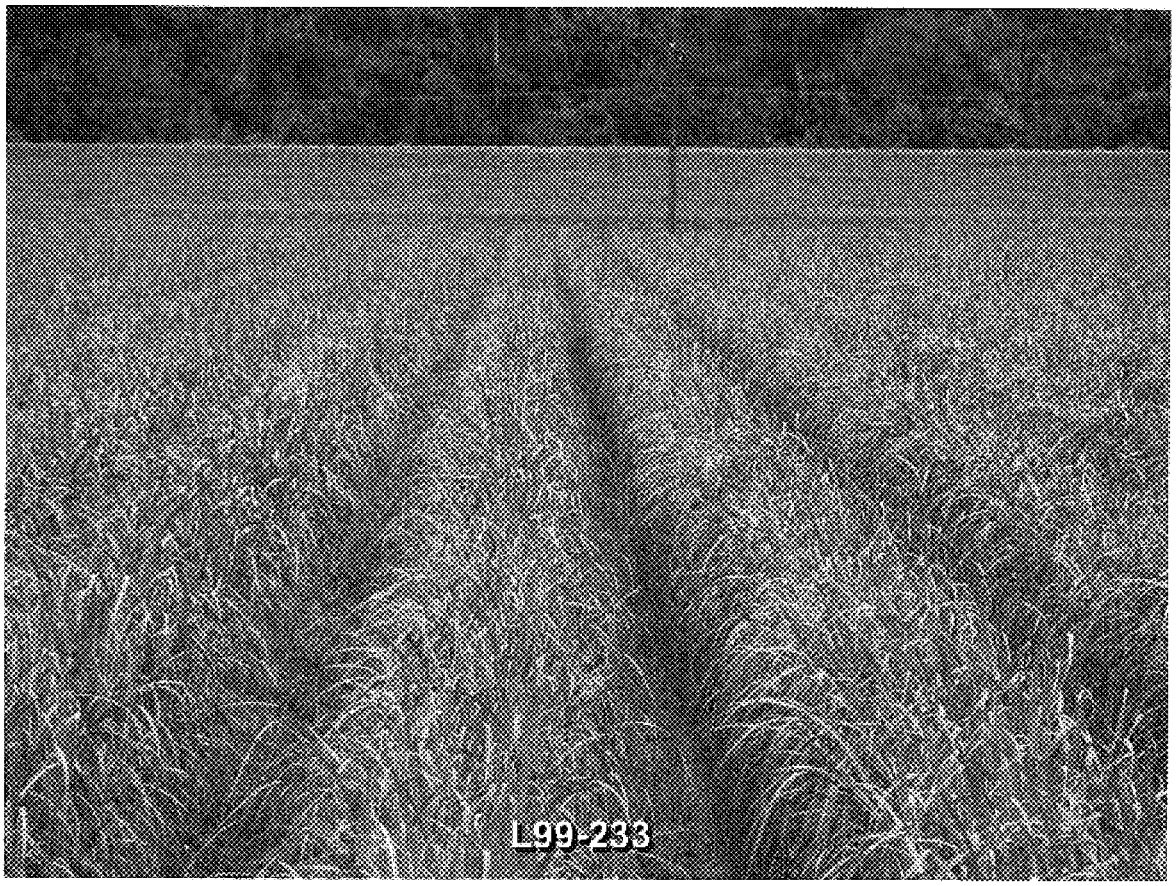
FIG. 5 is a color photograph of a plant cane crop of 'L99-233' in early May, 2006 in Plaquemine, La.

FIG. 5 depicts early spring growth habit of 'L99-233'. The canopy structure of 'L99-233' in early spring was erect plants with drooping leaves, which was characteristic throughout the growing season. Stalks of 'L99-233' lodged easily as growth approached late summer and early fall.

Under normal growing conditions in Louisiana, 'L99-233' does not flower. The following flower description was obtained from a 38 L can culture of 'L99-233' grown in St. Gabriel, La. on Sep. 28, 2006 (approximately 130–145 days in age from spring emergence). Each inflorescence (tassel) had a main axis and later axes of first, second, and third order. 'L99-233' exhibited a cylindrical-shaped inflorescence peduncle, degenerating from the base, having a width and length of approximately 5.50 mm and 40–50 mm, respectively, and pubescence throughout, with short, appressed, silvery pilose hairs [R (red)-Y (yellow) 9/10Y (yellow)]. 'L99-233' had a 530–540 mm long inflorescence main axis with some pilose hairs. Primary branches of 'L99-233' were 270–315 mm long and exhibited appressed racemose branches. Rachis internodes of 'L99-233' were glabrous from the bottom of the main axis, and exhibited a few setaceous hairs towards the apex of the main axis. The apex of 'L99-233' was predominantly grooved. Each spikelet had a single flower comprising three or four glumes, two lodicules, a whorl of three stamens, and a single ovary with two feathery stigmas. Sessile spikelets of 'L99-233' were 4.0–4.5 mm long with white [R (red)-Y (yellow) 9/10Y (yellow)] callus hairs having lengths of 9–10 mm. The sessile spikelets of 'L99-233' were lanceolate, acuminate, and have membranous glumes, lemma with a hyaline scale, and stamens 2.5–3.0 mm long consisting of a purple anther 2.5 R (Red) 2/6 and a filament [R (red)- Y (yellow) 9/10Y (yellow)]. Pedicellate spikelets of 'L99-233' are ovate, acute, rounded at the base, and 5.0–6.0 mm long. The glumes of the pedicillate spikelets of 'L99-233' are membranous; lemmas were hyaline; and stamens were comprised of a purple [2.5 R (Red) 2/6] anthers and white filaments [R (red)- Y (yellow) 9/10Y (yellow)]. See G. C. Stevenson. 1965. Flowering in Sugar Cane. pp. 72–97. In: Genetics and Breeding of Sugar Cane. Tropical Science Series. Longmans, Green and Co. Ltd., London.

Example 1

Test Conducted

To confirm that 'L99-233' was a new variety, controlled tests (e.g., pathogen responses and yield), wee conducted in St. Gabriel, La. Fifty mechanically harvested, outfield variety trials conducted across south Louisiana involving the replication of 'LCP85-384', 'HoCP91-555', 'HoCP96-540', 'L 97-128', and 'L99-226' were selected from comparison tests with 'L99-233' because of their commercial dominance or potential in the Louisiana sugarcane market. The parents of 'L99-233' were not included in the yield trails. Diseases that commonly affect the growth of sugarcane were selected to test for pathogen responses in all the varieties. 'L99-233' like its male parent 'HoCP91-552', exhibited similar moderate resistance to sugarcane mosaic and sorghum mosaic viruses. The female parent, 'CP79-348', is susceptible to sugarcane mosaic and sorghum mosaic viruses. 'L99-233', 'CP79-348', and 'HoCP91-552' exhibited moderate resistance to smut (caused by *Ustilago scitaminea* Sydow & P. Sydow). 'L99-233' and 'HoCP91-552' similarly exhibited resistance to rust (caused by *Puccinia melanocephala* H. and P. Sydow), whereas 'CP79-348' exhibited moderate resistance to this disease. 'L99-233', 'CP79-348', and 'HoCP91-552' similarly exhibited moderate resistance to leaf scald (caused by *Xanthomonas albilineans* Ashby, Dowson), under natural field infection conditions. The effect of yellow leaf disease on the yield of 'L99-233' and its parents is unknown. Similar to both of its parents, 'L99-233' exhibited significant yield loss in ratoon crops from ratoon stunting disease (caused by *Calvibacter xyli subsp. xyli* Davis). 'L99-233' was susceptible to the sugarcane borer (caused by *Diatraea saccharalis* Fabricius), whereas 'HoCP91-552' had a moderate rating for resistance to the sugarcane borer. The reaction of 'CP79-348' to sugarcane borer is unknown. Field observations show that 'L99-233' was no more susceptible to herbicides commonly used for weed control than other commercial sugarcane varieties grown in Louisiana. Sugarcane disease and sugarcane borer ratings of 'L99-233', 'CP79-348', and 'HoCP91-552' are shown in Table 2.

No other formal trails have been conducted to date on 'L99-233' for other insect pests. 'L99-233' does not appear to show any novel insect resistance.

TABLE 2

| Variety | Mosaic | Smut | Rust | Leaf Scald | Ratoon Stunting Disease | Sugarcane Borer |
|---|---|---|---|---|---|---|
| 'L99-233' | MR | MR | R | MR | S | S |
| 'CP79-348' | S | MR | MR | MR | S | U |
| 'HoCP91-552' | MR | MR | R | MR | S | M |
| 'HoCP91-555' | R | R | MS | MR | S | S |
| 'Ho95-988' | R | MS | MS | MR | MS | S |
| 'HoCP96-540' | R | R | MR | R | MS | S |
| 'L97-128' | R | MS | MR | MR | S | S |

"R"—Resistant; "MR"—Moderately Resistant; "M"—Moderate; "S"—Susceptible; "MS "—Moderately Susceptible; and "U"—Unknown To determine yield, fifty mechanically harvested, outfield variety trails involving the replication of 'L99-233', 'LCP85-384', 'HoCP91-555', 'HoCP96-540', 'L97-128', and 'L99-226' were conducted between the years 2003 and 2005 at various locations within Louisiana. The varieties were planted in Balwin silt clay loam in St. Mary Parish, Commerce silt loam in Pointe Coupee Parish, Commerce silt loam in St. James Parish, Commerce silt loam in Lafourche Parish, Commerce silt loam in Assumption Parish, Jeanerette silt loam in Iberia Parish, Patout silt loam in St. Martin Parish, Commerce silt loam in St. John the Baptist Parish, and Sharkey clay in Terrebonne Parish. Each block/plot was fertilized with nitrogen, potassium, and phosphorous according to standard farm practices associated with each operation. 'L99-233' produced an average fiber content of 13.2% after twenty-three trials, which was higher than the 11.9% average fiber content produced by 'LCP 85-384'. Data for sugar yield, cane yield, sucrose content, stalk weight, and stalk population are shown in Table 3.

TABLE 3

| Variety | Sugar Yield (Mt/ha) | Cane Yield (Mt/ha) | Sucrose Content [%)/Mt] | Stalk Weight (kg) | Stalk Population (stalks/ha) |
|---|---|---|---|---|---|
| | | Plant-cane crop (26)† | | | |
| 'LCP85-384' | 8.20 | 60.3 | 13.6 | 0.85 | 72,581 |
| 'HoCP91-555 | 9.15+ | 65.2+ | 14.0+ | 0.90+ | 74,265 |
| 'HoCP96-540' | 9.92+ | 71.0+ | 14.0+ | 1.09+ | 67,384– |
| 'L97-128' | 9.19+ | 65.9+ | 14.0+ | 1.07+ | 62,091– |
| 'L99-226' | 10.63+ | 71.9+ | 14.8+ | 1.25+ | 59,290– |
| 'L99-233' | 6.69+ | 71.0+ | 13.7 | 0.86 | 85,385+ |
| | | First ratoon crop (17)† | | | |
| 'LCP85-384' | 7.54 | 55.6 | 13.7 | 0.69 | 81,757 |
| 'HoCP91-555 | 8.76+ | 61.2+ | 14.3+ | 0.78+ | 79,124 |
| 'HoCP96-540' | 8.91+ | 63.4+ | 14.1+ | 0.88+ | 73,455– |
| 'L97-128' | 8.50+ | 60.5+ | 14.1+ | 0.89+ | 68,135– |
| 'L99-226' | 9.72+ | 65.2+ | 15.0+ | 1.03+ | 63,929– |
| 'L99-233' | 8.77+ | 63.4+ | 13.9 | 0.72 | 89,582+ |
| | | Second ratoon crop (7)† | | | |
| 'LCP85-384' | 6.80 | 50.0 | 13.6 | 0.63 | 80,258 |
| 'HoCP91-555 | 6.69 | 48.8 | 13.7 | 0.63 | 76,506 |
| 'HoCP96-540' | 7.41 | 54.7 | 13.6 | 0.77+ | 70,877 |
| 'L97-128' | 7.72 | 56.7+ | 13.6 | 0.76+ | 73,633 |
| 'L99-226' | 8.93+ | 58.7+ | 15.1+ | 0.90+ | 65,816– |
| 'L99-233' | 8.33+ | 65.3+ | 13.3 | 0.63 | 98,242+ |

†Number in parentheses represents the total number of trials. Varieties that are significantly higher or lower than 'LCP85-384' are denoted by a plus (+) or minus (–), respectively. The analysis was performed using the SAS (v 9.0) statistical software package (SAS Institute Inc., Cary, North Carolina).

First ratoon maturity tests were conducted in Chacahoula, La. to compare the percentage of sucrose content per ton of cane of 'L99-233', LCP 85-384', 'HoCP85-845', 'HoCP91-555', 'Ho95-988', 'HoCP96-540', 'L97-128', and 'L99-226', 'L99-233' demonstrated early maturity with above average values at the first three sampling dates, equal to the test average at the fourth sampling date, and slightly below average for the last three sampling dates, as shown in Table 4. Compared with all varieties across all sampling dates, 'L99-233' was slightly higher than the overall average (12.3% vs. 12.2%), as shown in Table 4.

TABLE 4

| | 2005 Harvest Dates | | | | | | | Ave. by |
|---|---|---|---|---|---|---|---|---|
| Variety | 9/12 | 9/28 | 10/12 | 10/24 | 11/07 | 11/21 | 12/05 | Variety |
| | % Recovery per Mt | | | | | | | |
| LCP85-384 | 7.8 | 9.5 | 11.0 | 12.6 | 14.0 | 14.7 | 15.2 | 12.1 |
| HoCP85-845 | 9.2 | 10.5 | 11.3 | 13.0 | 13.6 | 13.7 | 14.5 | 12.3 |
| HoCP91-555 | 8.0 | 10.0 | 12.0 | 13.1 | 13.8 | 14.8 | 14.8 | 12.4 |
| Ho95-988 | 7.7 | 9.5 | 10.7 | 12.6 | 13.4 | 13.9 | 15.1 | 11.8 |
| HoCP96-540 | 8.2 | 9.6 | 10.6 | 12.5 | 13.3 | 14.5 | 15.0 | 11.9 |
| L97-128 | 9.7 | 10.8 | 11.8 | 12.8 | 13.9 | 14.5 | 14.6 | 12.6 |
| L99-226 | 8.6 | 9.8 | 10.7 | 13.1 | 14.4 | 15.1 | 15.7 | 12.5 |

TABLE 4-continued

| Variety | 2005 Harvest Dates | | | | | | | Ave. by Variety |
|---|---|---|---|---|---|---|---|---|
| | 9/12 | 9/28 | 10/12 | 10/24 | 11/07 | 11/21 | 12/05 | |
| | % Recovery per Mt | | | | | | | |
| L99-233 | 9.1 | 10.9 | 11.9 | 12.7 | 13.4 | 14.0 | 14.5 | 12.3 |
| Ave. by Date | 8.6 | 10.1 | 11.3 | 12.7 | 13.6 | 14.2 | 14.7 | 12.2 |

We claim:

1. A new and distinct variety of *Saccharum* sp. plant named 'L99-233', as described and illustrated in the specification herein.

* * * * *